Figure 1:
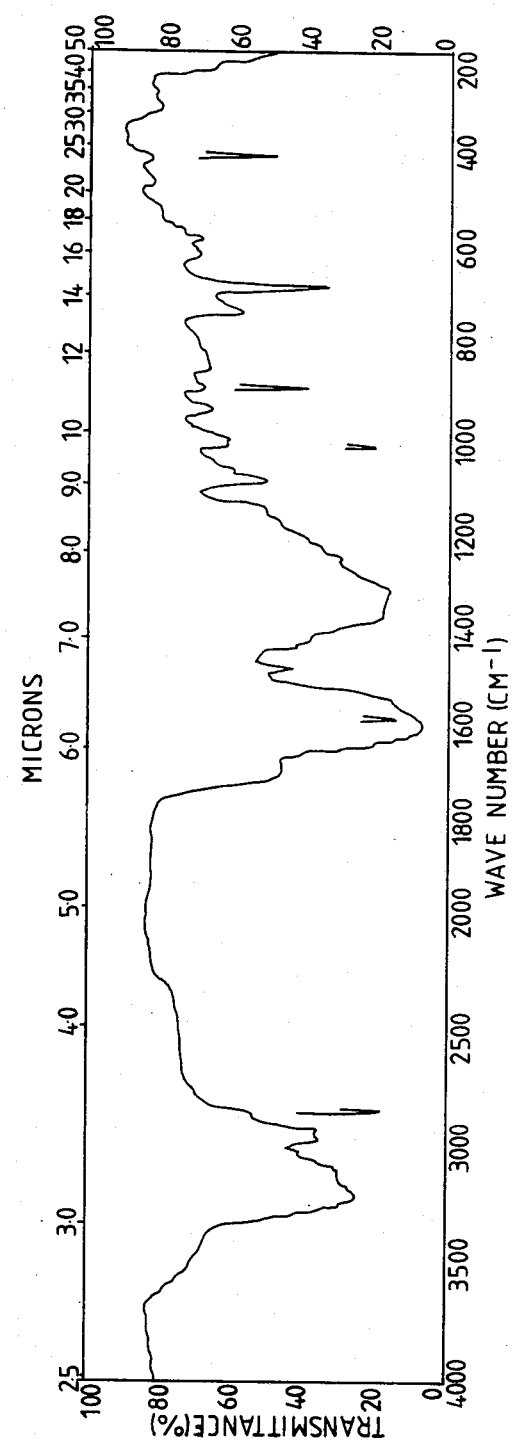

United States Patent [19]

Barnard

[11] Patent Number: 4,687,780
[45] Date of Patent: Aug. 18, 1987

[54] ANTI-TUMOR COMPOUNDS OF PLATINUM

[75] Inventor: Christopher F. J. Barnard, Reading, England

[73] Assignee: Johnson Matthey PLC, London, England

[21] Appl. No.: 746,155

[22] Filed: Jun. 18, 1985

[51] Int. Cl.$^4$ .................. A01N 55/04; A61K 31/32; C07F 15/00
[52] U.S. Cl. .................................. 514/492; 556/137
[58] Field of Search .................... 556/137; 514/492

[56] References Cited

U.S. PATENT DOCUMENTS 4,053,587 10/1977 Davidson et al. ............... 514/492
4,140,707 2/1979 Cleare et al. .................... 556/137
4,203,912 5/1980 Hydes et al. .................... 556/137
4,329,299 5/1982 Hydes ............................. 556/137

Primary Examiner—Helen M. S. Sneed
Attorney, Agent, or Firm—Cushman, Darby & Cushman

[57] ABSTRACT

A coordination compound of platinum suitable for the treatment of cancer and especially for oral administration has the general formula

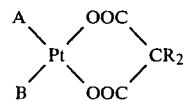

in which A is $NH_3$ or cycloalkylamine, B is cycloalkylamine, and the R moieties are the same or different selected from H, lower alkyl etc. or form a cycloalkyl or cycloalkenyl group with the C atom.

7 Claims, 5 Drawing Figures

ANTI-TUMOR COMPOUNDS OF PLATINUM

This invention relates to anti-tumor co-ordination compounds of platinum and to pharmaceutical compositions containing such compounds.

It has been known since the early 1970's that cis-diamminedichloroplatinum(II), known generically as cisplatin, is effective for the treatment of certain forms of malignant tumor in humans. However, it is also toxic and induces certain unpleasant side-effects, particularly nephrotoxicity. Much effort has been expended as a result in an attempt to find analogous compounds which are either effective over a broader spectrum of tumors, or are more active and/or less toxic than cisplatin. A paper by K. R. Harrap entitled "Platinum Analogues: Criteria for Selection" published in Cancer Chemotherapy, Vol. 1, 1983 reviews the development history of cisplatin and the various attempts so far to find effective second generation compounds. This paper reports that, by 1979, 1055 platinum complexes had been screened by the U.S. National Cancer Institute, although antitumor activity was demonstrated in only 18%. Certain guideline requirements for antitumour activity were proposed as a result but proved largely unreliable in practice. Nevertheless, Harrap reports that, although only very tentative and preliminary observations are as yet available from early clinical trials on selected analogues of cisplatin, the problem of nephrotoxicity has been largely circumvented in many of these derivatives although the problem of myelosuppression remains.

One particular class of analogues is described in U.K. Pat. No. 1380228 (Research Corp). This discloses various diamine or bis(amine) complexes of Pt(II) an Pt(IV) where the leaving group is substituted or unsubstituted malonate or a derivative thereof such as cyclobutanedicarboxylate. Where the amine moiety is a diamine it may be for example substituted or unsubstituted ethylene-diamine and where it is a bis(amine) it may be the same or different selected from ammine, lower alkylamines (normal and iso), arylamines, aralkylamines, hydroxy lower alkylamines, hydroxylamine, alkoxylamines, heterocyclic amines, and amino acids. Harrap reports screening data on three such compounds: diammine(2-hydroxymalonato)platinum(II) (known as JM-5), diammine(2-ethylmalonato)-platinum(II) (JM-10) and diammine(1,1-cyclo-butane(-dicarboxylato)platinum(II) (JM-8); the last-named has also been reviewed by Harrap on clinical trial. JM-5 and JM-10 were only moderately promising on screening results; JM-8 looked reasonably promising on a Phase I clinical trial although myelosuppression and to a lesser extent vomiting remained troublesome.

We have now found that certain amines other than those disclosed in GB 1380228 when used as ligands in co-ordination complexes of platinum also containing malonate and derivates thereof as leaving group ligand give promising results on initial screening against various tumors.

According to the invention, therefore, we provide a co-ordination compound of platinum having the general formula

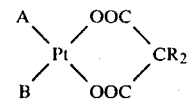

in which the A moiety is selected from ammine and cycloalkylamine, B is cycloalkylamine, and the R moieties are the same or different and are selected from H, lower alkyl, aryl, aralkyl, alkenyl, cycloalkyl, cycloalkenyl, alkoxy and OH or are combined with the host carbon atom to form a cycloalkyl or cycloalkenyl group, and substituted derivatives thereof.

The invention also includes a pharmaceutical composition comprising an effective amount of a co-ordination compound of platinum according to the above formula in admixture with a pharmaceutically-acceptable carrier, diluent or excipient. Such compositions may be suitable for oral or parenteral administration.

The invention also includes co-ordination compounds of platinum according to the above formula for use in the treatment of cancer, and a method of treatment of cancer using such compounds.

The cycloalkylamine moiety of compounds according to the invention has the general formula cyclo-$C_nR^1_{2n-1}NH_2$ in which n is an integer from 3 to 9, preferably 4 to 7, inclusive and the $R^1$ groups are preferably H but individual $R^1$ groups may represent lower alkyl, hydroxy, amino etc. substituent groups. Although compounds where the A and B groups are the same and are both cycloalkylamine are within the scope of the invention, we prefer to use compounds where the A group is amine. Such compounds are believed to give improved selectivity, lower toxicity and/or enhanced activity particularly against tumors which are resistant to treatment with other platinum compounds. Most preferred cycloalkylamines are cycloalkylamine, cyclopentylamine and cyclohexylamine.

The compounds according to the invention include the bidentate malonate or cycloalkyl- or cycloalkenyl-dicarboxylate ligand any of which may be substituted or unsubstituted. Substituent groups may be selected from lower alkyl (e.g. methyl, ethyl, isopropyl), aryl, aralkyl (e.g. benzyl), alkenyl, cycloalkyl, cycloalkenyl, alkoxy and hydroxy. Preferably the R groups both represent H, individually represent H and methyl, H and ethyl, H and benzyl or H and hydroxy, or together with the host carbon atom represent cyclobutanedicarboxylate.

Compounds according to the invention may in general terms be prepared by a two stage reaction which involves firstly the formation of the complex cis-(A)(B)PtI$_2$ and secondly conversion of this complex via an aquo complex to the desired end product.

Such a method constitutes a further aspect of the invention, as does the intermediate cis-(A)(B)PtI$_2$.

The preparation of various compounds according to the invention will now be described by way of example.

EXAMPLE 1

Preparation of ammine(benzylmalonato)(cyclobutylamine)platinum-(II)

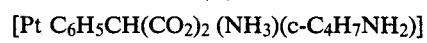

K[PtCl$_3$(NH$_3$)](15.0 g, 0.042 mol) was dissolved in water (80 ml), KI (20.90 g, 0.126 mole) in water (30 ml) was added and the dark solution stirred for 30 seconds. Cyclobutylamine (3.27 g, 0.046 mol) was added and immediately a bright yellow precipitate formed. The reaction mixture was allowed to stir for 1 hour and the product collected by filtration. The product was washed with water, then very well with ethanol until the washings were colourless, and finally with diethylether. The compound was dried in vacuo.

Yield = 15.3 g (68%)

$AgNO_3$ (9.25 g, 0.054 mol) was dissolved in water (30 ml) and cis-[$PtI_2(NH_3)(c-C_4H_7NH_2)$] (15 g. 0.028 mol) added portion-wise with rapid stirring. The suspension was stirred for 2.5 h at 45° C. in the dark, and then filtered. The filtrate was tested for $Ag^+$ ions (negative) and benzylmalonic acid (6.50 g, 0.034 mol) in water (10 ml) neutralised to pH6 was added. Immediately a mobile oil separated which slowly began to thicken and solidify. After solidification was complete the product was collected by filtration, washed with water and dried in vacuo.

The product was recrystallised from DMA/water, collected by filtration, washed with water and dried in vacuo.

Yield = 4.2 g (31.6%)

|  |  | Elemental Analysis | | | | |
| --- | --- | --- | --- | --- | --- | --- |
|  |  | C | H | N | O | Pt |
| $C_{14}H_{20}N_2O_4$ | req % | 36.37 | 4.21 | 5.89 | 13.47 | 41.05 |
|  | found % | 36.31 | 4.67 | 6.12 | — | — |

EXAMPLE 2

Preparation of ammine(cyclohexylamine)(tartronato)platinum(II) hydrate

$K[PtCl_3(NH_3)]$ (15.0 g 0.042 mol) was dissolved in water (110 ml), KI (20.90 g, 0.126 mol) in water (40 ml) was added and the dark solution stirred for 20 seconds. Cyclohexylamine (4.38 g, 0.044 mol) was added and immediately a bright yellow precipitate formed. The reaction mixture was allowed to stir for 1 hour and the product collected by filtration. The product was washed with water, then very well with ethanol until the washings were colourless, and finally with diethylether. The compound was dried in vacuo.

Yield = 14.0 g (59.0%)

$AgNO_3$ (8.30 g, 0.049 mol) was dissolved in water (30 ml) and cis-[$PtI_2(NH_3)(c-C_6H_{11}NH_2)$] (14 g, 0.049 mol) added portion-wise with rapid stirring. The suspension was stirred for 2.5 h at 45° C. in the dark, and then filtered. The filtrate was tested for $Ag^+$ ions (negative) and tartronic acid (4.45 g, 0.037 mol) in water (30 ml) adjusted to pH6 added. After stirring overnight the solution was reduced in volume and the product collected by filtration, washed with water, ethanol and diethylether, and dried in vacuo. A second crop was obtained.

Yield = 4.2 g (32%)

|  |  | Elemental Analysis | | | | |
| --- | --- | --- | --- | --- | --- | --- |
|  |  | C | H | N | O | Pt |
| $C_9H_{20}N_2O_6Pt$ | req % | 24.16 | 4.51 | 6.26 | 21.45 | 43.60 |
|  | found % | 24.66 | 4.14 | 6.30 | — | — |

EXAMPLE 3

Preparation of ammine(cyclobutane-1,1-dicarboxylato)cyclohexylamine platinum(II)

To a solution of $K[PtCl_3(NH_3)]$ (10 g. 0.028 mol) in water (100 ml) was added aqueous KI solution (13.94 g, 0.084 mol) and cyclohexylamine (2.97 g, 0.30 mol). After stirring for about 30 minutes the yellow precipitate was collected by filtration, washed thoroughly with water, ethanol and diethylether and dried in vacuo.

Yield = 8.71 g (59.29%)

The yellow solid was added, in a portion-wise fashion, to an aqueous solution of $AgNO_3$ (5.1 g, 0.03 mol). The resultant slurry was stirred and heated at 50° C. for 3 hours in the dark. The solution was filtered and the filtrate tested for the presence of $Ag^+$ ions. These being absent, charcoal (5 g) was added to the liquid and, after stirring for a few minutes, removed by filtration. Aqueous CBDCA (4.39 g, 0.030 mol) solution, which had previously been neutralised by the addition of KOH, was added in a single portion to the rapidly stirred filtrate. Stirring was continued for 96 hours after which the creamy white solid formed was removed by filtration, washed with water, ethanol and diethylether before being dried in vacuo at 20° C.

Yield = 4.57 g (68%)

|  |  | Elemental Analysis | | | | |
| --- | --- | --- | --- | --- | --- | --- |
|  |  | C | H | N | O | Pt |
| $C_{12}H_{22}N_2O_4Pt$ | req % | 31.78 | 4.85 | 6.18 | 14.11 | 43.02 |
|  | found % | 30.79 | 4.82 | 6.16 | — | — |

EXAMPLE 4

Preparation of ammine(cyclobutane-1,1-dicarboxylato)cyclopentylamine platinum(II)

To a solution of $K[PtCl_3(NH_3)].H_2O$ (10 g, 0.021 mol) in water (100 ml) was added aqueous KI solution (10.41 g. 0.062 mol) and cyclopentylamine (11.95 g, 0.022 mol). After stirring for about 30 minutes the yellow precipitate was collected by filtration, washed thoroughly with water, ethanol and diethylether and dried in vacuo.

Yield = 6.81 g (58.64%)

The yellow solid was added, in a portion-wise fashion, to an aqueous solution of $AgNO_3$ (4.19 g, 0.025 mol). The resultant slurry was stirred and heated at 50° C. for 3 hours in the dark. The solutions was filtered and the filtrate tested for the presence of $Ag^+$ ions. These being absent, charcoal (5 g) was added to the liquid and, after stirring for a few minutes, removed by filtration. Aqueous CBDCA (2.17 g, 0.047 mol) solution, which had been previously neutralised with KOH, was added in a single portion to the rapidly stirred filtrate. Stirring was continued for 96 hours after which the creamy white solid formed was removed by filtration, washed with water, ethanol and diethylether before being dried in vacuo at 20° C.

Yield = 4.19 g (77.6%)

| | | Elemental Analysis | | | | |
|---|---|---|---|---|---|---|
| | | C | H | N | O | Pt |
| $C_{11}H_{20}O_4N_2Pt$ | req % | 30.07 | 4.59 | 6.38 | 14.50 | 44.40 |
| | found % | 29.42 | 4.53 | 6.41 | — | — |

EXAMPLE 5

Preparation of ammine(ethylmalonato)(cyclohexylamine) platinum(II) dihydrate

cis-$[Pt\{C_2H_5CH(CO_2)_2\}(NH_3)(c-C_6H_{11}NH_2)].2H_2O$

To a solution of $K[PtCl_3(NH_3)]$ (15 g, 0.042 mol) in water (240 ml) was added KI(20.86 g. 0.126 mol) in water (45 ml) while rapidly stirring. Cyclohexylamine (4.15 g, 0.042 mol) was added and immediately an orange precipitate was formed. After stirring for a further 45 minutes the precipitate was filtered, washed sequentially with water, ethanol and diethylether, and dried in vacuo.

Yield = 11.93 g (43.4%)

$AgNO_3$ (4.76 g, 0.028 mol) was dissolved in water and cis-$[PtI_2(NH_3)(c-C_6H_{11}NH_2)]$ (7.91 g, 0.014 mol) was added. Stirring was continued for 2 hours, the solution was filtered, tested for $Ag^+$ ions and treated with charcoal. To the filtrate was added an aqueous solution of ethylmalonic acid (2.21 g, 0.017 mol) and KOH to pH6. Dropwise addition of KOH solution was continued for pH 7, the volume was reduced to approx 150 ml and, after standing for 2 hours, the white creamy precipitate was removed by filtration. A second crop was obtained by evaporating the filtrate. Analysis revealed the second crop to be predominantly inorganic nitrate.

Yield (1st crop) = 1.25 g (20.3%)

| | | Elemental analysis | | | | |
|---|---|---|---|---|---|---|
| | | C | H | N | O | Pt |
| $C_{11}H_{26}N_2O_6Pt$ | req % | 27.67 | 5.45 | 5.87 | 14.51 | 44.22 |
| | found % | 27.98 | 5.11 | 5.92 | — | — |

Figure 2:
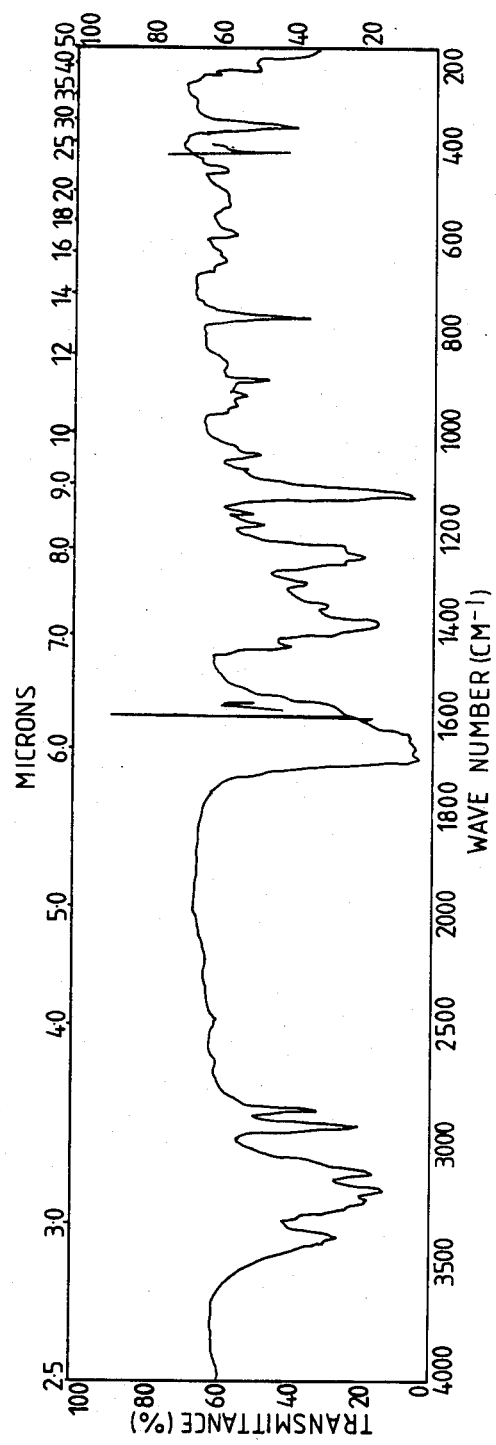
Figure 3:
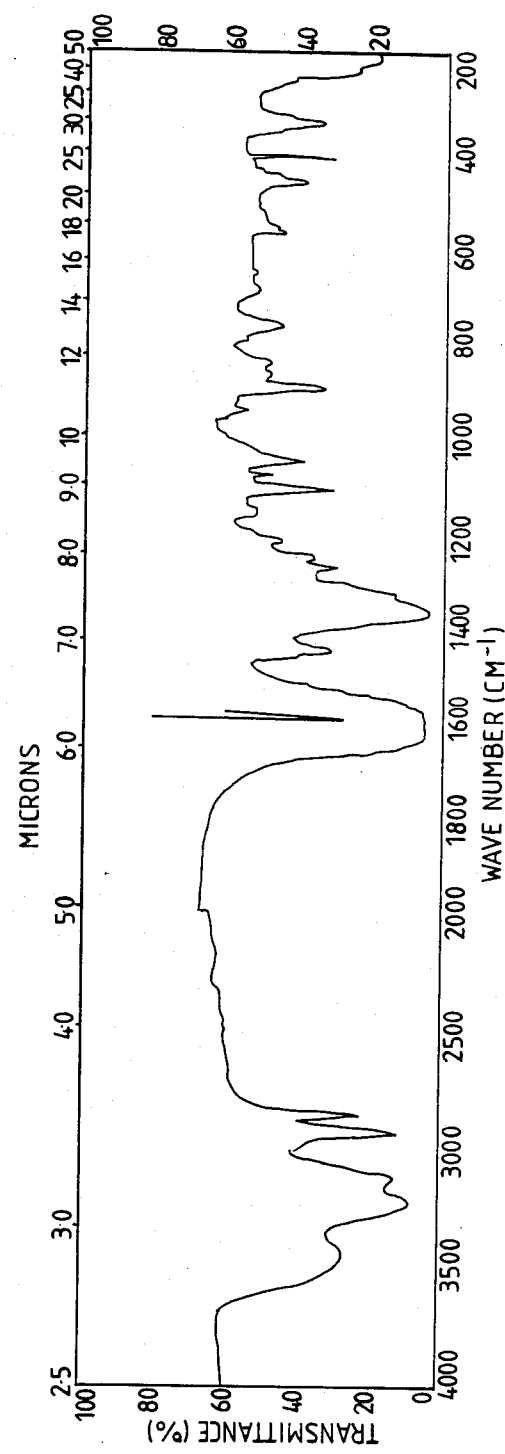
Figure 4:
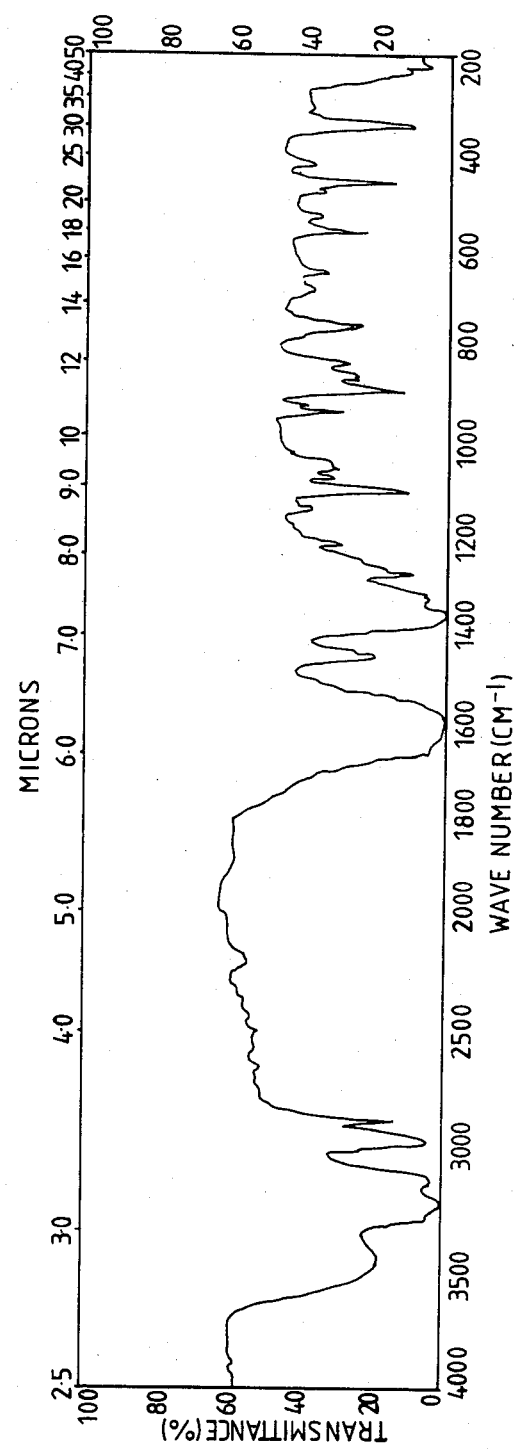
Figure 5:
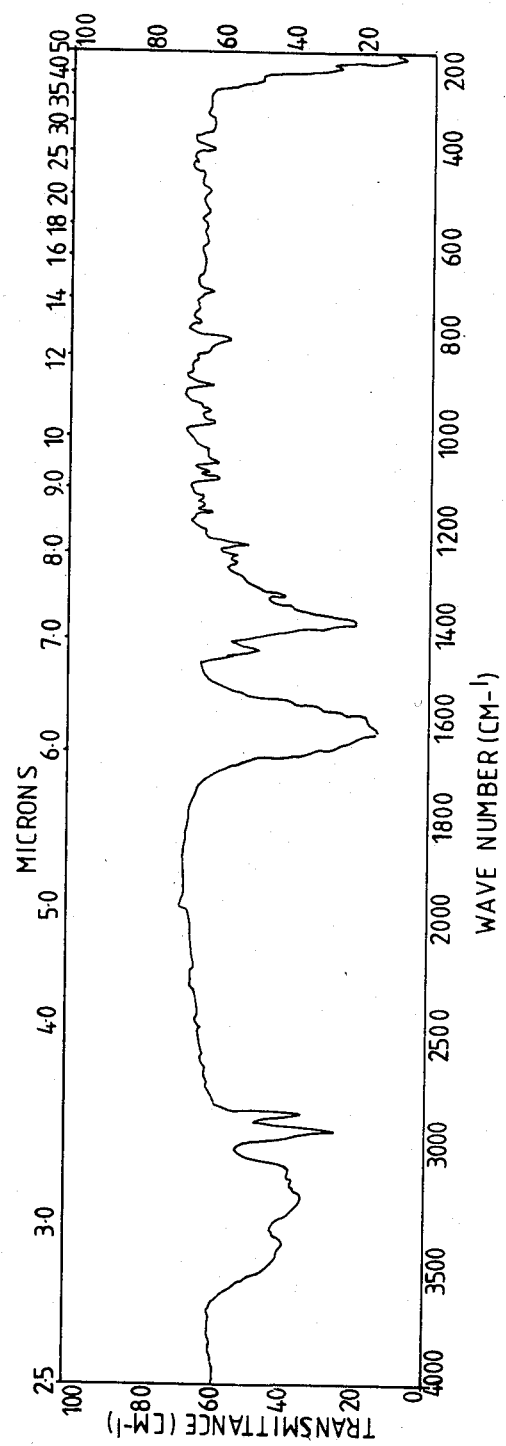

The infra-red spectra of the above compounds are shown in FIGS. 1 to 5 of the accompanying drawings.

Compounds according to the invention were screened for anti-tumor activity against L1210 leukaemia and B16 melanoma in mice. The compounds were administered intraperitoneally as solutions or suspensions in water and "Tween" 80 as carrier to CDF1 male mice (L1210) and BDF1 female mice (B16). Results were compared with cisplatin and JM-8 dissolved in biological saline and, as control, biological saline alone. For each dose level, results are quoted in terms of median survival time (MST); the comparative effect (i.e. MST/MST control × 100); average weight change (AWC) by Day 5 (L1210) or Day 6 (B16); and the number of mice alive (MA) at Day 5 (L1210) or Day 10 (B16).

Results were as follows for the compounds as prepared in Examples 3 and 4.

1. L1210 (1×10⁶ cells): treatment consisted of single dose on Day 1.

TABLE 1

| Compound | Dose (mg/kg) | MST | % T/C | AWC (g) | MA |
|---|---|---|---|---|---|
| Ex. 3 | 160 | 15.0 | 231 | −4.5 | 5/6 |

TABLE 1-continued

| Compound | Dose (mg/kg) | MST | % T/C | AWC (g) | MA |
|---|---|---|---|---|---|
| | 120 | 12.0 | 185 | −0.6 | 6/6 |
| | 80 | 12.0 | 185 | −2.4 | 6/6 |
| | 40 | 10.0 | 154 | −0.1 | 5/5 |
| Ex. 4 | 160 | 12.5 | 192 | −2.5 | 6/6 |
| | 120 | 11.5 | 177 | 0.0 | 6/6 |
| | 80 | 11.5 | 177 | −0.2 | 6/6 |
| | 40 | 10.0 | 154 | 0.5 | 6/6 |
| cisplatin | 10 | 8.0 | 123 | −4.7 | 6/6 |
| | 8 | 12.5 | 192 | −4.6 | 6/6 |
| | 6 | 11.0 | 169 | −3.2 | 6/6 |
| | 4 | 9.5 | 146 | −0.8 | 6/6 |
| JM-8 | 128 | — | 86 | — | — |
| | 64 | — | 150 | — | — |
| | 32 | — | 171 | — | — |
| | 16 | — | 143 | — | — |
| | 8 | — | 121 | — | — |
| | 4 | — | 100 | — | — |
| control | 0.5 ml | 6.5 | 100 | 1.6 | 10/10 |

2. B16 (0.5 ml 10% BREI): treatment consisted of 9 daily doses beginning at Day 1.

TABLE 2

| Compound | Dose (mg/kg) | MST | % T/C | AWC (g) | MA |
|---|---|---|---|---|---|
| Ex. 3 | 24 | 34.5 | 177 | −1.4 | 10/10 |
| | 18 | 34.0 | 174 | −1.6 | 10/10 |
| | 12 | 29.0 | 149 | −1.0 | 10/10 |
| | 6 | 26.5 | 136 | −0.3 | 10/10 |
| Ex. 4 | 30 | 32.0 | 164 | −1.2 | 10/10 |
| | 20 | 29.0 | 149 | −1.4 | 10/10 |
| | 13 | 26.0 | 133 | −1.1 | 10/10 |
| | 8 | 22.5 | 115 | −1.1 | 10/10 |
| cisplatin | 2.4 | 45.0 | 231 | −3.9 | 10/10 |
| | 1.6 | 36.5 | 187 | −3.1 | 10/10 |
| | 0.8 | 32.0 | 164 | −1.5 | 10/10 |
| | 0.4 | 25.5 | 131 | −0.9 | 10/10 |
| JM-8 | 32 | — | 176 | — | — |
| | 16 | — | 176 | — | — |
| | 8 | — | 150 | — | — |
| | 4 | — | 115 | — | — |
| | 2 | — | 112 | — | — |
| control | 0.5 ml | 19.5 | 100 | −1.2 | 10/10 |

Additionally, the same compounds were tested for activity against ADJ/PC6A plasmacytoma grown subcutaneously in female Balb $C^-$ mice following oral administration as a suspension in arachis oil. Dosage levels were at 100μ mole/kg of body weight for pharmacokinetic tests to establish the extent of absorption into the systemic circulation.

Results are presented in terms of concentration (μg/ml) of Pt in the blood and cumulative percentage dose in urine, cage wash and faeces, all after specified time intervals. Results for anti-tumor effect are expressed as $LD_{50}$ (mg/kg), $ED_{90}$ (mg/kg), and TI ($LD_{50}/ED_{90}$). The figures for $LD_{50}$ (the dose level causing 50% deaths) and $ED_{90}$ (the dose level causing a 90% reduction in tumor size) are determined by administering dosage levels ranging from lethal to non-tumor inhibitory. The therapeutic index (TI) is an indication of the selectivity of the compound as an anti-tumor agent.

TABLE 3

| | PHARMACOKINETIC TESTS | | | |
|---|---|---|---|---|
| | TIME | COMPOUND | | |
| TEST | (hrs) | Ex. 3 | Ex. 4 | JM-8* |
| Blood conc. | 1 | 0.62 ± 0.11 | 0.88 ± 0.05 | 2.4 |
| (μg/ml of whole | 2 | 0.80 ± 0.08 | 1.21 ± 0.16 | 1.7 |
| blood) | 4 | 0.64 ± 0.03 | 0.82 ± 0.12 | 0.72 |
| | 7 | 0.51 ± 0.09 | 0.32 ± 0.05 | 0.63 |
| | 24 | 0.16 ± 0.05 | 0.20 ± 0.03 | 0.25 |

TABLE 3-continued

| | PHARMACOKINETIC TESTS | | | |
|---|---|---|---|---|
| | TIME | COMPOUND | | |
| TEST | (hrs) | Ex. 3 | Ex. 4 | JM-8* |
| | 48 | 0.16 ± 0.03 | 0.20 ± 0.03 | 0.25 |
| Urine dose | 24 | 11.4 ± 2.1 | 16.8 ± 2.4 | 10.3 |
| (cumulative %) | 48 | 12.8 ± 1.8 | 18.2 ± 2.4 | 10.8 |
| Cage wash | 24 | 5.1 ± 1.2 | 7.1 ± 0.7 | — |
| (cumulative %) | 48 | 6.4 ± 1.8 | 8.0 ± 0.9 | — |
| Faeces dose | 24 | 57.0 ± 14.1 | 57.6 ± 3.5 | — |
| (cumulative %) | 48 | 62.1 ± 13.7 | 59.8 ± 3.6 | — |

*JM-8 was administered at a level of 50 mg/kg whereas a level of 100μ mole/kg would have required 37 mg/kg.

TABLE 4

| ANTITUMOR ACTIVITY | | | |
|---|---|---|---|
| Compound | $LD_{50}$ | $ED_{90}$ | TI |
| Ex. 3 | 1600 | 73 | 22 |
| Ex. 4 | 1600 | 50 | 32 |
| cisplatin | 140 | 24 | 5.8 |
| JM-8 | 235 | 99 | 2.4 |

It is shown by the above results that although compounds according to the invention show only a modest improvement over JM-8 against L 1210 and are marginally inferior againt B 16, both following parenteral administration, nevertheless the data for oral administration shows a clear superiority over JM-8. The pharmacokinetic data show a greater percentage dose excreted in the urine indicating a greater level of absorption. There is a very significant increase in anti-tumor effectiveness from an unacceptable therapeutic index of 2.4 to a satisfactory level of 20–30+. The effective dose ($ID_{90}$) is decreased indicating that these compounds have greater potency for this route of administration and the compounds are effectively non-lethal.

This data shows that compounds according to the invention offer equivalent or greater anti-tumor activity compared with other malonates but have lower toxicity. As a class they have adequate aqueous solubility, sufficient to be suitable for iv infusion as is used for conventional platinum drug therapy, but they also have significant advantages over current compounds in their potential for oral administration.

I claim:

1. A co-ordination compound of platinum having the general formula

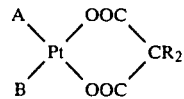

in which the A moiety is ammine and B is cycloalkylamine, and the R moieties are the same or different and are selected from H, lower alkyl, aryl, aralkyl, alkenyl, cycloalkyl, cycloalkenyl, alkoxy and OH or are combined with the host carbon atom to form a cycloalkyl or cycloalkenyl group.

2. A coordination compound of platinum according to claim 1 in which the cycloalkylamine moiety has the general formula cyclo-$C_nH_{2n-1}NH_2$ in which n is an integer from 4 to 7.

3. A coordination compound of platinum according to claim 2, wherein the A moiety is ammine and B is selected from cyclobutylamine, cyclopentylamine and cyclohexylamine.

4. A coordination compound of platinum according to claim 1, wherein the $(OOC)_2CR_2$ moiety is selected from malonato, benzylmalonato, ethylmonato, tartronato and cyclobutane-1,1-dicarboxylato.

5. A coordination compound of platinum according to claim 1 which is ammine(cyclobutane-1,1-dicarboxylato)cyclohexylamine platinum (II).

6. A coordination compound of platinum according to claim 1 which is ammine(cyclobutane-1,1-dicarboxylato)cyclopentylamine platinum (II).

7. A pharmaceutical composition comprising an effective amount of a co-ordination compound of platinum according to any of claims 1 to 6 in admixture with a pharmaceutically-acceptable carrier, diluent or excipient.

* * * * *